US006379677B1

(12) United States Patent
Klesius et al.

(10) Patent No.: US 6,379,677 B1
(45) Date of Patent: Apr. 30, 2002

(54) *STREPTOCOCCUS INIAE* VACCINE

(75) Inventors: Phillip H. Klesius, Auburn; Craig A. Shoemaker, Notasulga, both of AL (US); Joyce J. Evans, Chestertown, MD (US)

(73) Assignee: The United States of America as represented by the Secretary of the Department of Agriculture, Washington, DC (US)

( * ) Notice: Subject to any disclaimer, the term of this patent is extended or adjusted under 35 U.S.C. 154(b) by 0 days.

(21) Appl. No.: 09/513,143

(22) Filed: Feb. 25, 2000

(51) Int. Cl.⁷ .................... A61K 39/09; A61K 39/02; A61K 39/38; A01N 63/00; C07K 1/00
(52) U.S. Cl. .................... 424/244.1; 424/234.1; 424/184.1; 424/236.1; 424/93.44; 424/827; 435/170; 530/825; 530/350
(58) Field of Search ............... 424/244.1, 184.1, 424/234.1, 203.1, 93.3, 93.4, 93.1, 93.44, 236.1, 827; 530/825, 820, 350, 806; 435/170, 820

(56) References Cited

U.S. PATENT DOCUMENTS 5,151,023 A * 9/1992 Kuzuhara et al. ............. 424/89

OTHER PUBLICATIONS

Bromage et al. In: Abstracts of the 8th Congress of the International Society of Developmental and Comparative Immunology, (Eds) Raftos DA. Dev. Compar. Immunol. 24: S87, Abstract M7, Jul., 2000.*
Bercovier et al. Dev. Biol. Stand. 90: 153–160, 1997.*
Akhlaghi et al. J. Fish Dis. 19: 251–258, 1996.*
Eldar et al. Vaccine 13: 867–870, 1995.*
Eldar et al. Vet. Immunol. Immunopathol. 56: 175–183, 1997.*
Klesius et al. Bull. Eur. Assoc. Fish Pathol. 19: 39–41, Mar., 1999.*

* cited by examiner

Primary Examiner—S. Devi
(74) Attorney, Agent, or Firm—M. Howard Silverstein; Joseph A. Lipovsky; John D. Fado

(57) ABSTRACT

Safe and effective mono and polyvalent vaccines against *Streptococcus iniae* may be prepared from formalin-killed cells and concentrated extracellular products of Streptococcus iniae which include one or more of deposited strains NRRL B-30238 and NRRL B-30242. Intraperitoneal and intramuscular vaccination of tilapia show acquisition of effective immunity against homologous and heterologous isolates of *S. iniae*.

4 Claims, No Drawings

*STREPTOCOCCUS INIAE* VACCINE

BACKGROUND OF THE INVENTION

1. Field of the Invention

*Streptococcus iniae* is a causative agent for streptococcal disease which in turn affects a variety of cultured and wild fish and results in severe economic loss. In the United States, tilapia and hybrid striped bass production is estimated to lose 10 million dollars annually as the result of disease caused by this organism. Antibiotic treatment is ineffective and the need for a vaccine to control streptococcal disease is paramount.

This invention relates to the creation of a novel vaccine against *Streptococcus iniae* which, due to its specific antigenic composition, does in fact provide superior protection over existing commercial vaccines.

2. Description of the Prior Art

Tilapia (*Oreochromis niloticus*) production is subjected to heavy economic losses due to mortality caused by *Streptococcus iniae*. Antibiotic treatment is ineffective and the need for a vaccine is now paramount for the control of streptococcal disease. Vaccines have previously been developed against various Streptococcus and Enterococcus species utilizing strategies based on either intraperitoneal or intramuscular injection. Akhlaghi et al. (Comparison of Passive and Active Immunization of Fish against Streptococcus (Enterococcus);Journal of Fish Diseases;19:251–258;1996) demonstrated that passive immunization of fish was possible using antibodies against Streptococcus generated in sheep, rabbits and fish, however, this protection was of short duration (one month). Their studies suggest the importance of antibody in protective immunity to streptococcal disease. Few studies have examined antibody response prior to challenge (i.e. post vaccination). Eldar et al. (Development and Efficacy of a Vaccine against *Streptococcus iniae* Infection in Farmed Rainbow Trout; Vet. Immunol. Immunopathol. 1997 56:175–183) did measure antibody titer by agglutination in rainbow trout vaccinated with $3.0\times10^{11}$ CFU *S. iniae*/ml. Titers detected were low (1:20–30) and were only 1:1 after six months. However, they suggested protection was due to this weak but measurable humoral response. This formalin-killed *S. iniae* vaccine protected trout in both experimental and field conditions for up to four months.

A *S. difficile* formalin-killed vaccine was reported to protect tilapia against challenge with *S. difficile* (Eldar et al.; Vaccination with Whole-cell Vaccine and Bacterial Protein Extract Protects Tilapia Against *Streptococcus difficile* Meningocephalitis; Vaccine. 13(9) 867–870; 1995 and Bercovier et al., Immunization with Bacterial Antigens: Infections with Streptococci and Related Organisms; Fish Vaccinology, Dev. Biol. Stand. Vol. 90 (Liiehaug, G., Midlyng, P J & Brown, F. eds.) Karger, Basel, Switzerland pp. 153–160, 1997).

SUMMARY OF THE INVENTION

We have now discovered a means for the creation of novel vaccines that are safe and effective for the control of *Streptococcus iniae* in tilapia (*Oreochromis niloticus*). The vaccines comprise one or more killed isolates of *Streptococcus iniae* in the form of whole cells and concentrated extracellular products having molecular weights greater than 2 kDa. These vaccines are effective in providing long lasting acquired immunity in tilapia to *Streptococcus iniae*.

In accordance with this discovery, it is an object of the invention to provide a novel, highly protective, vaccine against *Streptococcus iniae* in tilapia.

It is also an object of this invention to provide both monovalent and polyvalent vaccines against *Streptococcus iniae* that are more efficacious than those previously used.

It is a further object of this invention to improve the viability and productivity of tilapia, striped bass and other fish species, and to reduce economic losses thereto caused by *Streptococcus iniae*.

Other objects and advantages of the invention will become readily apparent from the ensuing description.

Deposit of Biological Material

*Streptococcus iniae* isolates ARS-98-60 and ARS-98-T23 were deposited on Jan. 10, 2000 under the provisions of the Budapest Treaty in the Agricultural Research Service Culture Collection located at 1815 North University Street, Peoria, Ill. 61604, and have been assigned Deposit No.'s NRRL B-30238, and NRRL B-30242 respectively.

*Streptococcus iniae* isolate ARS-98-10 was deposited on Feb. 25, 2000 under the provisions of the Budapest Treaty in the Agricultural Research Service Culture Collection located at 1815 North University Street, Peoria, Ill. 61604, and has been assigned Deposit No. NRRL B-30264.

DETAILED DESCRIPTION OF THE INVENTION

"Vaccine" is defined herein in its broad sense to refer to any type of biological agent in an administratable form capable of stimulating a protective immune response in an animal inoculated with the vaccine. For purposes of this invention, the vaccine may comprise one or more killed isolates of *Streptococcus iniae* in the form of whole cells in combination with their concentrated extracellular products having molecular weights greater than 2 kDa. These vaccines are effective in controlling infection by *Streptococcus iniae* in a variety of fish when administered thereto. Vaccination also significantly reduced abnormal behavior and morphology. Without being limited thereto, the vaccine is especially beneficial for the treatment of fish, both domestic and exotic, including yellowtail, rainbow trout, eels, striped bass and their hybrids, sea bass, sea bream, turbot and tilapia.

The starting material for use in preparing the vaccines of the invention may be any isolate of *Streptococcus iniae*. Preferred strains include NRRL B-30238, and NRRL B-30242. While efficacy has been shown with both monovalent and polyvalent vaccines, polyvalent systems are preferred due to the indicated antigenic heterogeneity seen to exist in *S. iniae*.

The inventive vaccine is a killed cell preparation or bacterin which includes a concentrated fraction of the extracellular filtrate (cell-free culture fluid) having a molecular weight greater than 2 kDa. While not wishing to be bound to theory, it is Applicants' surmise that various low molecular weight components of the extracellular products of formalin killed *S. iniae* have an inhibitory effect upon the antigenicity of the bacterin suspensions. Concentration of the extracellular retentate thus substantially removes these inhibitory components and thus increases efficacy of the vaccine. To produce the vaccine, viable cells of *S. iniae* are exposed to formalin for a sufficient period of time to kill 100% of the cells. Typically formalin concentration would range from about 1% to about 5% (v/v), preferably from about 1% to about 3% (v/v).

Suitable exposure times for a particular formalin concentration to achieve 100% killing may be readily determined from lethal killing curves of % killed vs. time of treatment.

Propagation of *S. iniae* in preparation for treatment with formalin may be accomplished using conventional techniques and culture media known in the art.

Following culture in media, the cells are concentrated, for example, by centrifugation and the cell pellet and culture fluid separated. The filtrate, in the form of the cell-free culture fluid, is then concentrated by use of a 2 kDa molecular filter. Separation may be carried out to completion, with water added to resuspend the retentate. In the alternative, and presently preferred, separation may be carried out until there has been a 10 to 30 fold reduction in retentate volume, most preferably a 20 fold reduction in retentate volume. This leaves adequate water in the retentate so that suspension of the cell pellet occurs upon recombination with the retentate.

Appropriate ratios may be determinable by those skilled in the art, but are seen to typically range from about 5:1 (vol/vol) to about 15:1 (vol/vol), preferably about 10:1 (vol/vol).

Following resuspension of the cell pellet in the retentate, the killed *S. iniae* cells are prepared for administration by formulation in an effective immunization dosage to the fish. The dose may either be given as simply the retentate containing the resuspended killed cells, or may further include pharmaceutically acceptable carriers and adjuvants known in the art. An effective immunization dosage is defined herein as being that amount which will induce complete or partial immunity (elicit a protective immune response) in a treated animal against subsequent challenge with virulent *S. iniae*. Immunity is considered as having been induced in a population of treated animals when the level of protection for the population is significantly higher than that of an unvaccinated control group. The appropriate effective dosage can be readily determined by the practitioner skilled in the art. Typically, the vaccine will contain at least about $1\times10^7$ cells of *S. iniae*, preferably about $1\times10^8$ cells of *S. iniae*. Although greater amounts of cells may be administered, use of such higher levels is generally considered impractical.

The killed cells are prepared for administration by formulation in a pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein [in Basic & Clinical Immunology, Stites et al. (ed.), fifth edition, Lange Medical Publications, Los Altos, Calif., 1984, pages 282–285], the contents of which are incorporated by reference herein.

In accordance with a preferred embodiment, the killed cells may be incorporated into microparticles or microcapsules to prolong the exposure of the antigenic material to the subject animal and hence increase the duration of protective immunity. The microparticles and capsules may be formed from a variety of well-known inert, biocompatible matrix materials using techniques conventional in the art. Without being limited thereto, suitable matrix materials include natural or synthetic polymers such as alginates, poly(lactic acid), poly(lactic/glycolic acid), poly(caprolactone), polycarbonates, polyamides, polyanhydrides, polyortho esters, polyacetals, polycyanoacrylates, polyurethanes, ethtylene-vinyl acetate copolymers, polystyrenes, polyvinyl chloride, polyvinyl fluoride, poly(vinyl imidazole), chlorosulphonated polyolefins, polyethylene oxide, and particularly agar and polyacrylates. Examples of techniques for incorporation of materials into microparticles or encapsulation which may be used herein are described by Sparks [Microencapsulation, In: Kirk-Othmer Encyclopedia of Chemical Technology, third edition, John Wiley & Sons, New York, (1981) volume 15, pages 470–493], Kydonius [Controlled Release Technologies: Methods, Theories, and Applications, CRC Press, Cleveland, Ohio, 1980], Gombotz et al. [U.S. Pat. No. 5,019,400], or Beck [U.S. Pat. No. 4,919,929], the contents of each of which are incorporated by reference herein.

The vaccines of the invention may be administered to the subject animal by any convenient route which enables the cells to elicit an immune response, such as by intraperitoneal or intramuscular injection. However, intraperitoneal injection is preferred for practical considerations. The vaccine may be administered in a single dose or in a plurality of doses. Dependent upon rearing conditions, the vaccine may be administered in multiple doses the timing of which would be readily determinable by the skilled artisan.

The following examples are intended only to further illustrate the invention and are not intended to limit the scope of the invention which is defined by the claims.

EXAMPLE 1

Materials and Methods

Tilapia from stocks maintained at the ARS, USDA, Aquatic Animal Health Research Laboratory (Auburn, Ala.) were used. Tilapia (mean weight of 18±2 g) were acclimated in flow-through 57 l glass aquaria supplied with 0.5 l/h dechlorinated water for 10 days prior to experiments. Five replicate tanks of 25 fish each were used in all immunization experiments. A light and dark period of 12 h :12 h was maintained and aeration was supplied by an air stone. The fish were fed daily to satiation with Aquamax Grower 400 (Brentwood, Mo.). To verify the *S. iniae*-free status of the fish, samples were obtained for bacterial culture by passing an inoculation loop into brain and kidney. Samples were streaked directly on sheep blood agar that were incubated at 27° C. for 24 to 48 h. *S. iniae* was not isolated from five randomly selected fish.

Water quality was monitored, with dissolved oxygen, temperature and salinity measured daily using a YSI 85 oxygen conductivity, salinity, and temperature meter (Yellow Spring Instrument Co., Yellow Springs, Ohio). The pH, hardness, ammonia and nitrites were determined daily using the Fresh Water Aquaculture Kit Model AG-2 (LaMotte., Chestertown, Md.). In all trials, the mean±standard deviation of dissolved oxygen (mg/l) was 6.02±0.561, temperature (°C.) was 25.4±0.627, pH was 7.2±0.0, salinity (%) was 0.1±0.00 and hardness was 110±10.0. Ammonia and nitrite concentrations (mg/l) were 0.

*Streptococcucs iniae* isolates NRRL B-30264 originally isolated from tilapia and NRRL B-30238 isolated from hybrid striped bass with natural streptococcal disease were used to infect fish. The isolates were identified as *S. iniae* by standard methods. Isolates were grown in tryptic soy broth (TSB, Difco Laboratories, Sparks, Md.) for 24 h at 27° C. and then were frozen in 0.2 ml aliquots at −70° C. The infectious isolates used in this study were prepared by inoculating 250 ml of TSB in 500 ml culture flask with a thawed aliquot of the frozen isolate. The cultures were adjusted to an optical density of 1.2 at 540 nm using a spectrophotometer to give a S. iniae concentration of $1 \times 10^8$ colony forming units (CFU)/ml (determined by plate count) after 24 h at 27° C. incubation. Fish were then challenged by IP injection of 100 µl S. iniae.

Vaccines were prepared by separate culture of Streptococcucs iniae isolates (NRRL B-30264 and NRRL B-30238) in tryptic soy broth (TSB) and incubated in a shaker (70 RPM) water bath at 27° C. for 72 hours. Cultures were treated with 10% neutral buffered formalin in to give a final concentration of 3% at 27° C. for 24 hours. The formalin treated cultures were centrifuged at 7000×g for 30 minutes and cell pellet and culture fluid separated. The cell free culture fluid was concentrated 20 fold using a 2 kDa hollow fiber concentrator to remove all components of lower molecular weight. This 2 kDa culture fluid concentrate was then used to re-suspend the cell pellet at V/V of 10:1. The final concentration of the vaccines were $4 \times 10^9$ CFU/ml (determined by previous plate count) or 1.9 optical density at 540 nm. The combined vaccine was produced using equal volumes of each vaccine NRRL B-30264 and NRRL B-30238. Non-vaccinates received concentrated tryptic soy broth (TSB) only. The vaccines were determined to be killed by lack of growth on sheep blood agar at 72 hours.

Vaccination Protocol

The NRRL B-30264 or the combined NRRL B-30264/NRRL B-30238 vaccines were either intraperitoneally (IP) or intramuscularly (IM) injected in a volume of 0.1 ml into tilapia. Control tilapia received 0.1 ml of TSB by either route. Immunized and control tilapia were held for 30 days before challenge. The tilapia were monitored for mortality for 14 days post-challenge as shown by Klesius et al. (Efficacy of a Killed Streptococcus Iniae Vaccine in Tilapia (Oreochromis niloticus); Bull. Eur. Ass. Fish Pathol., 19(1), 39;1999); herein incorporated by reference.

Bacteriologic Sample Collection and Evaluation

Dead fish were removed twice a day and at postmortem examination, specimens were obtained aseptically from brain and kidney sites. Specimens were cultured directly onto sheep blood agar at 27° C. for 24 to 48 h. Beta-hemolytic, catalase-negative and Gram-stained positive coccus colonies were subcultured onto sheep blood agar and then bacteriologically and biochemically identified as S. iniae according to tests described by Shoemaker and Klesius (Streptococcal Disease Problems and Control-A Review. In "Tilapia Aquaculture Vol. 2" (Fitzsimmons, K., ed.) Northeast Regional Agricultural Engineering Service, Ithaca, N.Y. Pp. 671–682;1997); herein incorporated by reference, all tests were conducted at 27° C. using media purchased from Remel (Lenexa, Ks.).

Data involving mortality, behavioral and morphological score were recorded on a daily behavioral and morphological checklist that included mortality, location of fish in the aquarium, swimming pattern, feeding response, activity/excitability and morphology. For the purpose of this study, one or more fish in an aquarium exhibiting behavioral and morphological signs of S. iniae were graded according to the following system:

0: normal behavior or morphology.
   1: surface or bottom location; any form of erratic swimming; slow acceptance of food; hyperactive, lethargic or unresponsive; and darkened skin coloration.
   2: No acceptance of food and eye opacity or body curvature.

The accumulative score was calculated as the mean score of five aquaria per treatment at 14 days post-challenge. The efficacy of the vaccine was calculated as the relative percent survival (RPS) according to Amend (1981).

Blood Collection and Serologic Evaluation

Blood samples were collected by venipuncture, placed into a micro-centrifuge tube and allowed to clot for 1 h at 25° C. and then centrifuged at 1,000×g for 10 min. Serum was collected by pasteur pipette and stored in a plastic-capped tube at −70° C. until assayed for antibody titer.

Antibody titer against Streptococcucs iniae in serum was determined by use of a microtitration agglutination test. Briefly, each well of a 96-round well microtitration plate was plated with 50 µl of phosphate-buffered saline (PBS) solution ( pH 7.2 to 7.4) and then 50 µl of tilapia serum was added to the first well of each row, mixed and then 50 µl of diluted serum was serially diluted into the remaining wells. Doubling dilutions of positive and negative sera were included on every plate as controls. To each well, 50 µl of S. iniae cells (NRRL B-30238) suspension was added and mixed. The plate was covered and incubated in humidified air at 25° C. for 18 h. The highest serum dilution that showed a circular diffuse button with fuzzy edges at the bottom of the well was considered a positive reaction and a circular compact cell button was considered to be a negative reaction. Antibody titer was expressed as log $base_{10}$ for each isolate studied.

Statistical Analysis

Mortality and behavioral and morphological data were analyzed by one way-analysis of variance using Duncan's multiple-range test (SAS Institute Inc., 1997). Relative percent survival (RPS) and antibody titer values were analyzed by Pearson correlation coefficient (SAS Institute Inc., 1997). Significant differences were determined at $P<0.05$ and $P<0.01$.

Results

Tilapia IP immunized and challenged with the homologous S. iniae NRRL B-30264 isolate had a mean percent mortality of 34.4 and RPS of 45.6 (Table 1). In contrast, the mean percent mortality was 52.0 and the RPS was 17.7 by the IM route of immunization (Table 1). Heterologous isolate challenge with the NRRL B-30238 isolate of tilapia IP immunized resulted in a RPS of 93.7. Tilapia IM immunized and then challenged with the heterologous S. iniae NRRL B-30238 isolate had a RPS of 59.5. Statistically there was a significant ($P<0.05$) difference in the mean percent mortality between IP and IM routes of immunization. The NRRL B-30264 vaccine administered only by IP route provided significant protection against both the homologous and heterologous S. iniae isolates. Mortality began at 4 days post challenge in the IP and IM NRRL B-30264 vaccinates and the non-vaccinates control fish, however the IP vaccinates had significantly ($P<0.05$) less mortality than the control fish at 14 days post challenge. Fish vaccinated by the IM route showed significantly decreased mortality only with NRRL B-30238 isolate challenge at 14 days. However, IM immunization of tilapia with a combined NRRL B-30264/NRRL B-30238 vaccine had RPS of 63.1 against S. iniae NRRL B-30264 and 87.3 against S. iniae NRRL B-30239 isolates (Table 1).

TABLE 1

Mortality and antibody titer of *Streptococcus iniae* vaccinated and non vaccinated tilapia after challenge with *S. iniae*[1].

| *S. iniae* vaccine | Route | Challenge isolate | Accumulative mortality | Mean percent mortality (SEM) | RPS | *S. iniae* titer (mean log base$_{10}$)[2] |
|---|---|---|---|---|---|---|
| NRRL B-30264 | IP | NRRL B-30264 | 43 | 34.4 (±0.7)[c] | 45.6 | −2.8896[e] |
| NRRL B-30264 | IP | NRRL B-30238 | 4 | 4.0 (±0.7)[e] | 93.7 | −3.0702[e] |
| NRRL B-30264 | IM | NRRL B-30264 | 65 | 52.0 (±1.3)[a] | 17.7 | −2.6087[de] |
| NRRL B-30264 | IM | NRRL B-30238 | 32 | 25.6 (±1.0)[d] | 59.5 | −2.7893[de] |
| NRRL B-30264 + NRRL B-30238 | IM | NRRL B-30264 | 29 | 23.3 (±1.8)[b] | 63.1 | −2.2337[cd] |
| NRRL B-30264 + NRRL B-30238 | IM | NRRL B-30238 | 10 | 8.0 (±0.7)[e] | 87.3 | −2.0067[bc] |
| TSB[3] | Control | NRRL B-30264/ NRRL B-30238 | 79 | 63.2 (±1.4)[a] | NA | −1.2441[a] |

[1]Accumulative mortality at 14 days post challenge or 44 days post-immunization. Tilapia with an average weight of 18 ± 2 g were stocked at 25 fish per tank into 5 replicate tanks for each treatment respectively.
[2]Mean serum antibody titer at 14 days post challenge and different superscripts indicate significant differences at the 95% level.
[3]Non vaccinates received tryptic soy broth (TSB) only.

The combined vaccine provided significant protection against the NRRL B-30264 isolate where monovalent NRRL B-30264 vaccine provided none. The mean percent mortality of the non-vaccinates was 63.2%.

Highly significant differences (P<0.01) were noted between the accumulative behavioral and morphological scores of the vaccinates and non-vaccinates (Table 2).

TABLE 2

Accumulative behavioral and morphological scores in vaccinates and non-vaccinates challenged with *S. iniae*[1].

| *S. iniae* vaccine | Route | Challenge isolate | Mean accumulative score[2] |
|---|---|---|---|
| NRRL B-30264 | IP | NRRL B-30264 | 9.2[bcd] |
| NRRL B-30264 | IP | NRRL B-30238 | 4.4[d] |
| NRRL B-30264 | IM | NRRL B-30264 | 12.4[b] |
| NRRL B-30264 | IM | NRRL B-30238 | 8.2[bcd] |
| NRRL B-30264 + NRRL B-30238 | IM | NRRL B-30264 | 8.8[bcd] |
| NRRL B-30264 + NRRL B-30238 | IM | NRRL B-30238 | 5.6[cd] |
| TSB[3] | Control | NRRL B-30264/ NRRL B-30238 | 27.8[a] |

[1]Mean accumulative behavioral and morphological socre at 14 days post challenge or 44 days post-immunization. Tilapia with an average weight of 18 ± 2 g were stocked at 24 fish per tank into 5 replicate tanks for each treatment respectively.
[2]Different superscripts indicate significant differences at the 95% level.
[3]Non vaccinates received tryptic soy broth (TSB) only.

The vaccinates had a 70.9% reduction in their mean score. A highly significant difference was also noted between vaccinates administered the NRRL B-30264 and the route of immunization. The behavioral and morphological score for IP vaccinates was 4.4 in comparison to a score of 12.4 for IM vaccinates. There was a highly significant negative correlation between the behavioral and morphological score and RPS®=−0.99, P=0.0003). The behavioral and morphological signs observed in the control non-vaccinates included surface or bottom erratic swimming, refusal of food, lethargic activity, darkening skin coloration and eye opacity. Vaccinates exhibited normal feeding and less frequent signs of abnormal behavior and morphology.

Statistical analysis of anti-streptococcal titer revealed significant differences (P<0.05) between vaccinates and non-vaccinates (Table 1). No significant (P>0.05) differences in anti-streptococcal titers were noted in the vaccinates between the routes of immunization and *S. iniae* isolates used for challenge. The NRRL B-30264/NRRL B-30238 combined vaccine stimulated slightly lower titers than did the single NRRL B-30264 isolate vaccine. Antibody titer and RPS values among the IP and IM vaccinates did not correlate®=0.09).

Discussion

Vaccination with *S. iniae* vaccine by IP injection resulted in acquired immunity against infection with homologous and heterologous *S. iniae* isolates. Intraperitoneal injection of the single isolate vaccine produced RPS of 45.6 and 93.7 against homologous and heterologous *S. iniae* isolates, respectively. However, differences exist between IP and IM routes of administration in their ability to induce protective immunity against the homologous and heterologous isolates. The results of IM injection were RPS of 17.7 and 59.5 against the homologous and heterologous *S. iniae* isolates, respectively. The basis for this difference is unknown, but differences in antigens between these two isolates are suggested. Tilapia IM vaccinated with the combined vaccine of both isolates had significantly enhanced protection compared to the single isolate vaccine following challenge with the homologous and heterologous isolates. Vaccination significantly (P<0.05) reduced abnormal behavior and morphology. Thus, the ability to prevent streptococcal disease by the *S. iniae* vaccine administered IM was significantly (P<0.05) increased by combining the two *S. iniae* isolates.

EXAMPLE 2

Materials and Methods

Tilapia

The vaccine trials were conducted in a temperature-controlled laboratory using flow-through 55-L glass aquaria. Tilapia (*O. niloticus*) with mean weights of 25 and 100 g were stocked in groups of 100 and 25 fish per aquarium, respectively. Three groups of 100 g tilapia were vaccinated and two groups of 100 g tilapia served as their non vaccinated controls. One group of 25 g tilapia were vaccinated and one group of 25 g tilapia served as their non vaccinated control. In all trials, water flow rate was adjusted to 0.5 L/minute and photo-period was maintained on a 12:12 hour light:dark schedule. Daily water temperature averaged 26° C. and mean daily dissolved oxygen was 5.5±0.7 mg/L. The tilapia were fed daily with Purina Catfish Chow (Purina Mills Inc., St. Louis, Mo.) at a rate of 4% body weight.

Vaccine Preparation

Streptococcucs iniae isolate NRRL B-30264 isolated from tilapia was cultured in trypic soy broth (TSB) and incubated in a shaker (70 RPM) water bath at 27° C. for 72 hours. Cultures were treated with 10% neutral buffered formalin to give a final concentration of 3% at 27° C. for 24 hours. The formalin treated culture was centrifuged at 7,000×g for 30 minutes and cell pellet and culture fluid separated. The cell-free culture fluid was concentrated 20 fold using a 2 kDa hollow fiber concentrator, filter sterilized (0.2 μm) and used to re-suspend the cell pellet at V/V of 10:1. The final concentration of the vaccine was $4 \times 10^9$ CFU/ml (determined by previous plate count) or 1.9 optical density at 540 nm. The vaccine was determined to be killed by lack of growth on sheep blood agar at 72 hours.

Vaccination Protocol

The vaccine was intraperitoneally (IP) injected in volumes of either 0.1 and 0.2 ml into tilapia of a mean weight of 25 and 100 g, respectively. Control tilapia were IP injected with sterile TSB at the same volumes.

Experimental Challenge

Vaccinated and non vaccinated groups of tilapia were challenged by IP injection with 0.1 ml of the S. iniae NRRL B-30264 isolate at cell concentration of $1 \times 10^9$ CFU/ml. The tilapia were challenged 30 days post vaccination. Mortalities were monitored twice daily during 60 days post challenge, and kidneys from dead tilapia were cultured to confirm the presence of S. iniae. Infected tilapia were also observed for behavioral and pathological signs of erratic swimming, hemorrhagic exophthalmia and ocular opacity. The efficacy of the vaccine was calculated as relative percent survival (RPS) (Amend, 1981).

Results

Results of the vaccine efficacy tests are shown in Table 3. Some non vaccinates of both weight groups died 1 day post challenge without behavioral or pathological signs. The remaining non vaccinates showed behavioral and pathological signs of S. iniae infection that began on day 4–5 post challenge. These behavioral and pathological signs were erratic swimming, hemorrhagic exopthalmia and ocular opacity. Non vaccinates mortality continued to 12 days post challenge. No further mortality was seen for the remaining 60 days. The mean percent mortality was 80.7 for all non vaccinates. In the vaccinates, deaths only occurred between 1 and 12 days after challenge. The mean percent mortality was 7.0 for all vaccinates. No behavioral or pathological signs were observed in the vaccinates. Vaccination reduced mean mortality 86.7 percent. The vaccinated groups of 25 and 100 g tilapia had relative percent survival's (RPS) of 95.3 and 84.2, 90.0 and 94.7, respectively (Table 3).

TABLE 3

Mortality of Streptococcus iniae vaccinated and non vaccinated tilapia after challenge with S. iniae.

| Tilapla groups- mean weigh (g) | Route and amount | No. of fish challenged | Mortality | Percent mortality | RPS |
|---|---|---|---|---|---|
| 25 | IP – 0.1 mL | 100 | 4 | 4.0 | 95.3 |
| 25 | Control | 100 | 86 | 86.0 | — |
| 100 | IP – 0.2 mL | 25 | 2 | 8.0 | 90.0 |
| 100 | Control | 25 | 20 | 80.0 | — |
| 100 | IP = 0.2 mL | 25 | 1 | 4.0 | 94.7 |
| 100 | IP – 0.2 mL | 25 | 3 | 12.0 | 84.2 |
| 100 | Control | 25 | 19 | 76.0 | — |

DISCUSSION

The results of this study show that 25 and 100 g tilapia were protected against S. iniae after IP immunization with the combined whole cell and extracellular product vaccine. Vaccination suppressed behavioral and pathological signs and mortality due to S. iniae infection. The vaccine was administrated without adjuvant nor booster. The adverse reactions of adjuvant were avoided by the use of this vaccine.

Surface antigens of Streptococcus are recognized as potential candidates for vaccines (Fishchetti, 1997). We hypothesize that extracellular products from S. iniae cultures consist principally of these surface antigens and that these antigens are involved in pathogenesis. The vaccine formulation provided very strong protection against S. iniae challenge of tilapia for at least 60 days.

Results of previous streptococcal bacterin studies clearly demonstrated only weak antibody responses (Eldar et al., 1995, Eldar et al., 1997, Bercovier et al., 1997). The mechanism(s) of immunity needs to be determined for the bacterin-extracellular product vaccine in tilapia. Tilapia age and/or size did not appear to influence the degree of protection provided by vaccination.

It is concluded that vaccination is effective when the bacterin was formulated using killed whole cells and concentrated greater then 2 kDa extracellular products. The excellent RPS indicated that the extracellular products combined with whole cells may be important for the development of efficacious S. iniae vaccines.

It is understood that the foregoing detailed description is given merely by way of illustration and that modification and variations may be made therein without departing from the spirit and scope of the invention.

We claim:

1. A composition comprising a dosage of formalin-killed whole cells of Streptococcucs iniae and concentrated extracellular products therefrom having a molecular weight greater than 2 kDa effective to immunize a fish against Streptococcucs iniae.

2. The composition of claim 1 wherein said Streptococcucs iniae include at least one strain selected from the group consisting of NRRL B-30238 and NRRL B-30242.

3. The composition of claim 1 wherein said cells and the extracellular products are from two strains of Streptococcus iniae.

4. The composition of claim 1 further including a pharmaceutically acceptable carrier.

* * * * *